(12) United States Patent
Liu et al.

(10) Patent No.: US 11,518,972 B2
(45) Date of Patent: Dec. 6, 2022

(54) MOVABLE CELL INCUBATOR

(71) Applicant: Lun-Kuang Liu, Hsinchu (TW)

(72) Inventors: Lun-Kuang Liu, Hsinchu (TW); Yung-Chin Chen, Hsinchu (TW)

(73) Assignee: Lun-Kuang Liu, Hsinchu (TW)

( * ) Notice: Subject to any disclaimer, the term of this patent is extended or adjusted under 35 U.S.C. 154(b) by 932 days.

(21) Appl. No.: 16/357,760

(22) Filed: Mar. 19, 2019

(65) Prior Publication Data

US 2019/0211295 A1 Jul. 11, 2019

Related U.S. Application Data

(63) Continuation-in-part of application No. 15/604,941, filed on May 25, 2017, now abandoned.

(51) Int. Cl.
| | |
|---|---|
| *C12M 1/00* | (2006.01) |
| *C12M 1/02* | (2006.01) |
| *C12M 1/107* | (2006.01) |
| *C12M 1/34* | (2006.01) |
| *C12M 1/12* | (2006.01) |
| *C12M 1/36* | (2006.01) |

(52) U.S. Cl.
CPC ............ *C12M 23/52* (2013.01); *C12M 23/14* (2013.01); *C12M 23/22* (2013.01); *C12M 23/36* (2013.01); *C12M 29/12* (2013.01); *C12M 37/00* (2013.01); *C12M 41/00* (2013.01); *C12M 41/14* (2013.01); *C12M 41/18* (2013.01); *C12M 41/34* (2013.01); *C12M 41/44* (2013.01); *C12M 41/48* (2013.01)

(58) Field of Classification Search
CPC .............................. C12M 41/14; C12M 23/52
See application file for complete search history.

(56) References Cited

U.S. PATENT DOCUMENTS

| | | | | |
|---|---|---|---|---|
| 3,860,309 A | * | 1/1975 | Brendgord | B65D 43/161 312/351 |
| 4,250,266 A | * | 2/1981 | Wade | C12M 27/10 435/286.2 |
| 4,701,415 A | * | 10/1987 | Dutton | C12M 41/14 55/467 |

(Continued)

FOREIGN PATENT DOCUMENTS

| | | |
|---|---|---|
| CN | 106566772 A | 4/2017 |
| TW | I567190 | 1/2017 |

*Primary Examiner* — Jonathan M Hurst
(74) *Attorney, Agent, or Firm* — Tomanageip (57) ABSTRACT

A movable cell incubator contains: a body, a first lid, a second lid and an electric control unit. The body includes a first internal space, a refrigeration room, and an airtight culture room. The first lid airtightly covers the culture room, the second lid airtightly covers the refrigeration room, and the control unit includes a microprocessor, a power module, a digital/analog conversion module defined between a microprocessor and the power module, a heating module controlling temperature of the culture room, a cooling module supplying cold source to the refrigeration room, a peristaltic pump module, a flow sensing module, a CO2 detective supply module supplying CO2 to the culture room, and a setting display module exposing and fixed on the first lid, with the peristaltic pump module aseptically connected between cell culture media and cell culture bag by multiple conveying tubes.

21 Claims, 7 Drawing Sheets

(56) References Cited

U.S. PATENT DOCUMENTS

| | | | | |
|---|---|---|---|---|
| 5,061,448 | A * | 10/1991 | Mahe | C12M 27/16 422/566 |
| 5,360,741 | A * | 11/1994 | Hunnell | B01L 7/00 422/561 |
| 5,418,131 | A * | 5/1995 | Butts | C12M 41/14 422/123 |
| 5,424,209 | A * | 6/1995 | Kearney | C12M 23/42 435/303.1 |
| 5,455,175 | A * | 10/1995 | Wittwer | B01L 7/52 422/417 |
| 5,577,837 | A * | 11/1996 | Martin | C12M 41/48 366/147 |
| 5,792,427 | A * | 8/1998 | Hugh | E06B 7/231 55/467 |
| 5,958,763 | A * | 9/1999 | Goffe | B01L 7/02 435/303.1 |
| 8,216,830 | B2 * | 7/2012 | Kobayashi | C12M 37/00 435/303.1 |
| 8,383,397 | B2 * | 2/2013 | Wojciechowski | C12M 41/34 417/474 |
| 8,822,210 | B2 * | 9/2014 | Baumfalk | C12M 27/16 366/115 |
| 2006/0194193 | A1 * | 8/2006 | Tsuruta | C12M 41/36 435/287.1 |
| 2010/0062522 | A1 * | 3/2010 | Fanning | C12M 41/14 435/303.1 |
| 2011/0315783 | A1 * | 12/2011 | Baker | B01L 1/025 236/3 |
| 2016/0201022 | A1 * | 7/2016 | Ozaki | C12M 23/52 435/325 |

* cited by examiner

MOVABLE CELL INCUBATOR

CROSS REFERENCE TO RELATED APPLICATIONS

This application is a continuation-in-part application of patent application Ser. No. 15/604,941, filed on May 25, 2017.

BACKGROUND OF THE INVENTION

1. Field of the Invention

The present invention relates to cell incubation, especially relates to a cell incubator which is compact and is movable easily.

2. Description of the Prior Art

With development of biological technology, cultivating autologous cells is a highlight issue in recently years. To cultivate cells in a sterile environment, the cells are cultivated in an aseptic culture room. However, maintaining culturing condition of the aseptic culture room is difficult.

It is expensive to build a large culture room, for example, the large culture room is established in large hospitals, biochemistry institutes, or organized inspection institutes. However, it will take times for patients to go to these hospitals, biochemistry institutes, and organized inspection institutes.

The present invention has arisen to mitigate and/or obviate the afore-described disadvantages.

SUMMARY OF THE INVENTION

The primary objective of the present invention is to provide a movable cell incubator which is compact and is movable easily.

Another objective of the present invention is to provide a movable cell incubator which automatically cultivates cells at designated time and quantity.

To obtain the above objectives, a movable cell incubator provided by the present invention contains: a body, a first lid, a second lid, and an electric control unit.

The body includes a first internal space, a refrigeration room and an airtight culture room which are located above the first internal space. The refrigeration room is configured to accommodate a culture fluid, and the culture room accommodating at least one cell culture bag.

The first lid rotatably connected on the body and airtightly covering the culture room. The second lid rotatably connected on the body adjacent to the first lid and airtightly covering the refrigeration room.

The electric control unit is arranged on the body, and the electric control unit including a microprocessor, a power module accommodated in the electric control unit, a digital/analog conversion module defined between the microprocessor and the power module, a heating module secured on an outer wall of the culture room and controlling a temperature of the culture room, a cooling module disposed on the electric control unit on an outer wall of the body and electrically connected with electric control unit so as to supply cold source to the refrigeration room, a peristaltic pump module, a flow sensing module, a $CO_2$ detective supply module arranged in the culture room and electrically connected with the microprocessor so as to supply $CO_2$ to the culture room, and a setting display module exposing and fixed on the first lid.

The peristaltic pump module is connected between the culture fluid and the at least one cell culture bag by way of multiple conveying pipes, the flow sensing module is serially connected on the multiple conveying pipes, the power module supplies power, and the setting display module is configured to set cell cultivating conditions, the microprocessor operates and controls the cell cultivating conditions, the flow sensing module detects fluid flow, and the peristaltic pump module pumps the culture fluid into the at least one cell culture bag.

The flow sensing module is coupled with the microprocessor and includes a flow meter and an infrared transceiver, wherein the flow meter has an inlet segment connected to the peristaltic pump module, an outlet segment coupled to the at least one cell culture bag, and a fan impeller, wherein the infrared transceiver has a transmitting portion and a receiving portion which face the fan impeller.

In another embodiment, the body comprises a culture room for accommodating a cell culture bag; a refrigeration room for accommodating a container of culture fluid; a pump chamber; and a first internal space located below the culture room. The first lid rotatably connected on the body and airtightly covering the culture room. The second lid rotatably connected on the body and airtightly covering the refrigeration room. The movable cell incubator further comprises a microprocessor, located in the first internal space; a setting display module, exposing and fixed on the first lid and coupled to the microprocessor, for displaying setting information and receiving cell cultivating condition from user; a peristaltic pump module, located in the pump chamber and coupled to the microprocessor, for connecting the container via a first conveying pipe and pump the culture fluid out of the container; a flow sensing module; and a power module. The flow sensing module further comprises a flow meter, having an inlet segment connected to the peristaltic pump via the first conveying pipe, an outlet segment connected to the cell culture bag via a second conveying pipe, and a fan impeller which rotates by the culture fluid pumped by the peristaltic pump; and an infrared transceiver, coupled to the microprocessor, having a transmitting portion and a receiving portion facing the fan impeller for detecting rotation of the fan impeller in order to report culture fluid flow inside the flow meter to the microprocessor. The power module, located in the first internal space, is configured for supplying power to the microprocessor, the setting display module, the peristaltic pump module, and the flow sensing module. The microprocessor is configured for controlling the setting display module and the peristaltic pump module according to the cell cultivating condition and the reported fluid flow.

Furthermore, the movable cell incubator may further comprises: a digital/analog conversion module, located in the first internal space and coupled to the microprocessor, for converting digital signal to analog signal and vice versa, wherein the digital/analog conversion module transmits and receives digital signal from the microprocessor; a heating module, secured on an outer wall of the culture room and coupled to the digital/analog conversion module, for heating the culture room; a fluid heating module, installed around the second conveying pipe and coupled to the digital/analog conversion module, for heating the second conveying pipe; a fluid temperature sensing module, installed around the second conveying pipe and coupled to the digital/analog conversion module, for sensing temperature of the second conveying pipe; a cooling module, disposed on an outer wall of the body and coupled to the digital/analog conversion module, for supplying cold source to the refrigeration room; a $CO_2$ detective supply module, arranged in the culture room and coupled to the microprocessor, for supplying CO2 to the culture room; and a temperature sensing module, having multiple sensors, wherein one of the multiple sensors is fixed on a central position of the culture room and another of the multiple sensors is fixed on the outer wall of the culture room so as to sense interior temperature and exterior temperature of the culture room, respectively. The power module is further configured for supplying power to the digital/analog conversion module, the heating module, the cooling module, the $CO_2$ detective supply module. The microprocessor is further configured for controlling the heating module, the fluid heating module, the cooling module, the CO2 detective supply module according to the cell cultivating condition and the exterior temperature and the interior temperature of the culture room.

The movable cell incubator provided by the present application may be small enough to be transported or carried by human. Cell cultivating process in the movable cell incubator can be setup in a aseptic laboratory or culture room. After sealing the movable cell incubators, they can be moved into a factory or a farm storing multiple movable cell incubators for mass production. Since the factory or the farm occupying large space is not required to be sterile or as clean as the aseptic laboratory or culture room, the incubating cost can be decreased dramatically.

In one embodiment, the aforementioned setup and seal steps follow GTP (Good Tissue Practice) requirements, which are written and enforced by U.S.A. Drug and Food Administration. The movable cell incubator provided by the present application also meets the GTP regulations, or the requirements of section 1271 of chapter 21 of the U.S. Code of Federation Regulations, entitled "Human Cells Tissues and Cellular and Tissue-Based Product". Because the movable cell incubator provides tightly closure and mobility, it can be moved to a place with less cleanliness and sanitation. The automated mechanism built in the movable cell incubator can be pre-programmed to provide culturing procedure in a certain time period to facilitate cell expansion procedure. It only takes multiple moveable cell incubators and a smaller facility following the GTP regulations for operating procedures to improve productivities significantly and to reduce costs of a large facility with environmental control.

The above description is only an outline of the technical schemes of the present invention. Preferred embodiments of the present invention are provided below in conjunction with the attached drawings to enable one with ordinary skill in the art to better understand said and other objectives, features and advantages of the present invention and to make the present invention accordingly.

BRIEF DESCRIPTION OF THE DRAWINGS

The present invention can be more fully understood by reading the following detailed description of the preferred embodiments, with reference made to the accompanying drawings, wherein.

DETAILED DESCRIPTION OF THE PREFERRED EMBODIMENTS

Some embodiments of the present invention are described in details below. However, in addition to the descriptions given below, the present invention can be applicable to other embodiments, and the scope of the present invention is not limited by such, rather by the scope of the claims. Moreover, for better understanding and clarity of the description, some components in the drawings may not necessary be drawn to scale, in which some may be exaggerated relative to others, and irrelevant parts are omitted.

Figure 12:
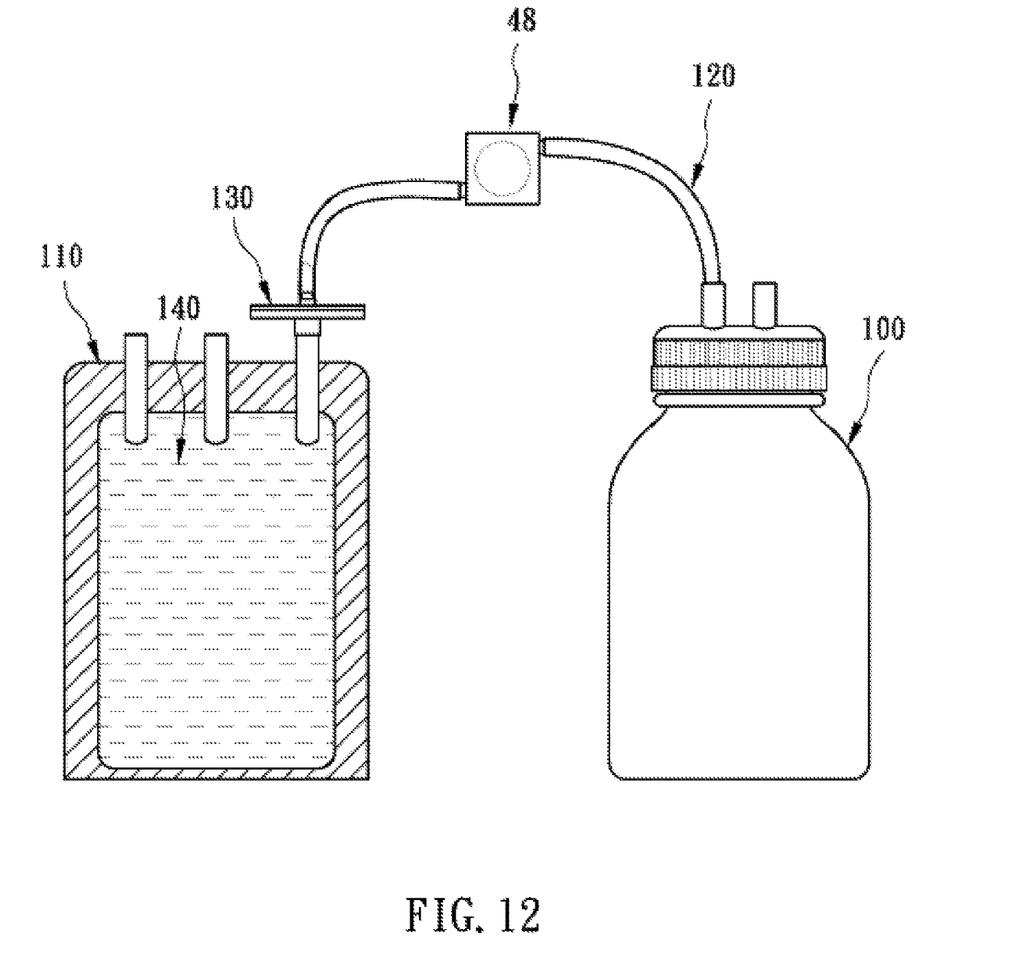
FIG. 12 is a cross sectional view showing a container connected with one of at least one cell culture bag via one of multiple conveying tubes on which a sterile filtering ring is fitted.

With reference to FIG. 12, a container 100 is connected with one of at least one cell culture bag 110 via one of multiple conveying tubes 120 on which a sterile filtering ring 130 is fitted, thus producing a sterile close system. The sterile close system is movable and is capable of refrigerating the container 100, maintaining temperature, and conveying fluids so as to cultivate cells successfully. The container 100 has a cell culture media 140 filled therein. In another embodiment, a container 100 may be connected with two or more cell culture bags 110.

Figure 1:
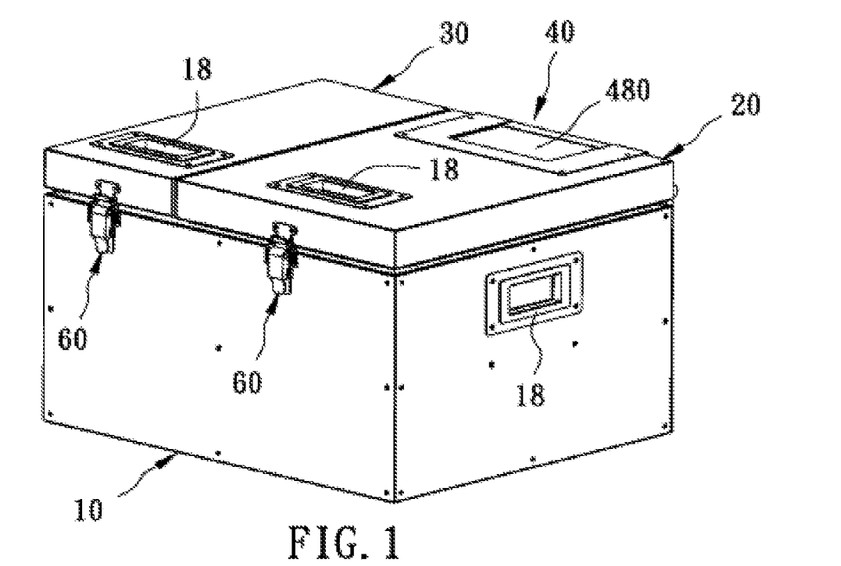
FIG. 1 is a perspective view showing the assembly of a movable cell incubator according to a preferred embodiment of the present invention.

Referring to FIG. 1, a movable cell incubator according to a preferred embodiment of the present invention comprises a body 10, a first lid 20, a second lid 30, and an electric control unit 40. The movable cell incubator is an integrated product of a mechanical structure and an electronic system for monitoring internal environments and controlling internal operations of the mechanical structure. In other words, the electric control unit 40 is the electronic system and the body 10, the first lid 20, and the second lid 30 constitute the mechanical structure.

The movable cell incubator provided by the present application may be small enough to be transported or carried by human. Cell cultivating process in the movable cell incubator can be setup in a aseptic laboratory or culture room. After sealing the movable cell incubators, they can be moved into a factory or a farm storing multiple movable cell incubators for mass production. Since the factory or the farm occupying large space is not required to be sterile or as clean as the aseptic laboratory or culture room, the incubating cost can be decreased dramatically.

In one embodiment, the aforementioned setup and seal steps follow GTP (Good Tissue Practice) requirements, which are written and enforced by U.S.A. Drug and Food Administration. The movable cell incubator provided by the present application also meets the GTP regulations, or the requirements of section 1271 of chapter 21 of the U.S. Code of Federation Regulations, entitled "Human Cells Tissues and Cellular and Tissue-Based Product". Because the movable cell incubator provides tightly closure and mobility, it can be moved to a place with less cleanliness and sanitation. The automated mechanism built in the movable cell incubator can be pre-programmed to provide culturing procedure in a certain time period to facilitate cell expansion procedure. It only takes multiple moveable cell incubators and a smaller facility following the GTP regulations for operating procedures to improve productivities significantly and to reduce costs of a large facility with environmental control.

Figure 2:
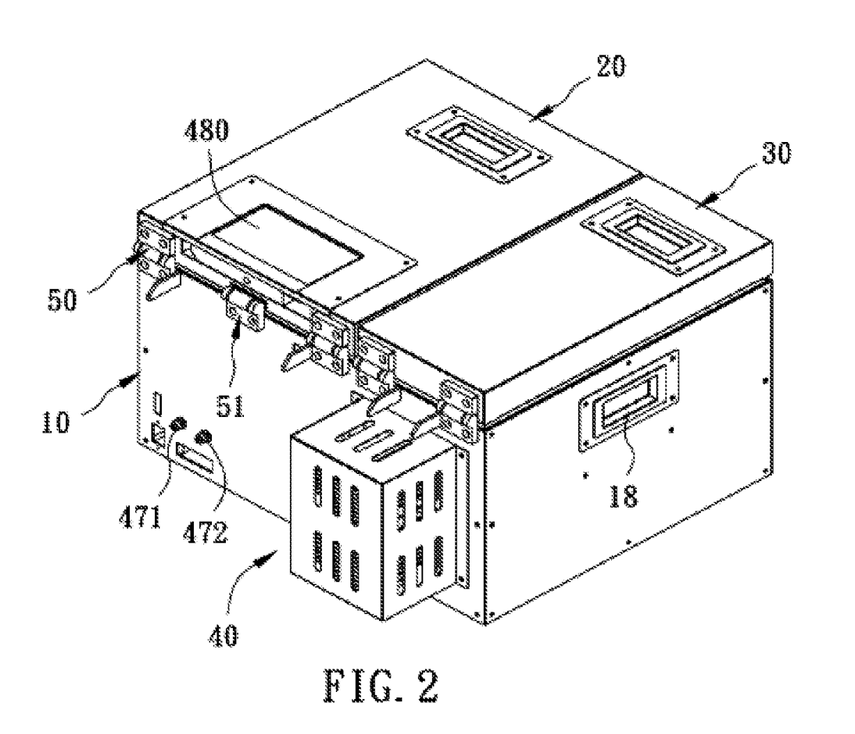
FIG. 2 is another perspective view showing the assembly of the movable cell incubator according to the preferred embodiment of the present invention.
Figure 5:
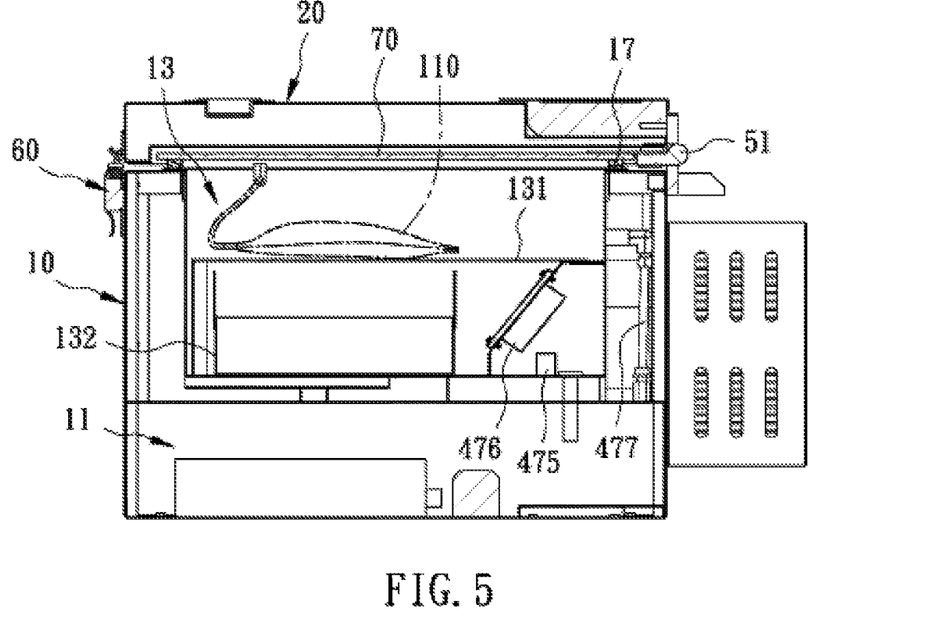
FIG. 5 is a cross sectional view showing the assembly of the movable cell incubator according to the preferred embodiment of the present invention.
Figure 6:
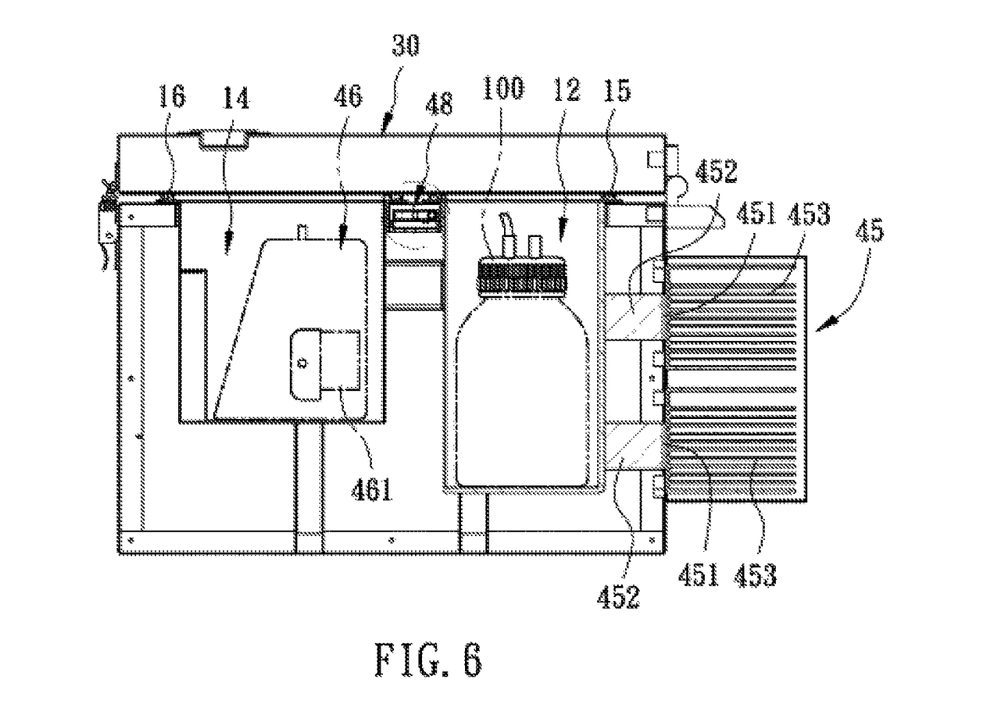
FIG. 6 is another cross sectional view showing the assembly of the movable cell incubator according to the preferred embodiment of the present invention.

As shown in FIGS. 2, 5, and 6, the body 10 includes a first internal space 11, a refrigeration room 12 and an airtight culture room 13 which are located above the first internal space 11, wherein the refrigeration room 12 is configured to store the container 100, and the culture room 13 accommodates the at least one cell culture bag 110.

The first lid 20 airtightly covers the culture room 13, and the second lid 30 airtightly covers the refrigeration room 12.

As illustrated in FIGS. 6-9, the electric control unit 40 includes a microprocessor 41, a power module 42, a digital/analog conversion module 43 defined between the microprocessor 41 and the power module 42, a heating module 44 for controlling a temperature of the culture room 13, a fluid heating module 144 for controlling a temperature of culture fluid, a cooling module 45 configured to supply cold source to the refrigeration room 12, a peristaltic pump module 46 having a step motor 461, a $CO_2$ (carbon-dioxide) detective supply module 47 configured to supply $CO_2$ to the culture room 13, a flow sensing module 48, a temperature sensing module 49 configured to measure temperature of the culture room 13, a fluid temperature sensing module 149 configured to measure temperature of the culture fluid, and a setting display module 480 exposing and fixed on the first lid 20. The microprocessor 41, the power module 42, and the digital/analog conversion module 43 are accommodated in the first internal space 11 of the body 10. The peristaltic pump module 46 is aseptically connected between the container 100 and the at least one cell culture bag 110 by way of the multiple conveying tubes 120, the flow sensing module 48 is serially connected on the multiple conveying tubes 120, the power module 42 supplies power, and the setting display module 480 is configured to set cell cultivating conditions. The microprocessor 41 operates and controls the cell cultivating conditions, the flow sensing module 48 detects fluid flow, and the peristaltic pump module 46 pumps the cell culture media 140 into the at least one cell culture bag 110 by way of the step motor 461. In one embodiment, the cell cultivating conditions include parameters such as culture fluid flow rate, temperature of the culture room, temperature of refrigeration room, and $CO_2$ concentration.

Figure 9:
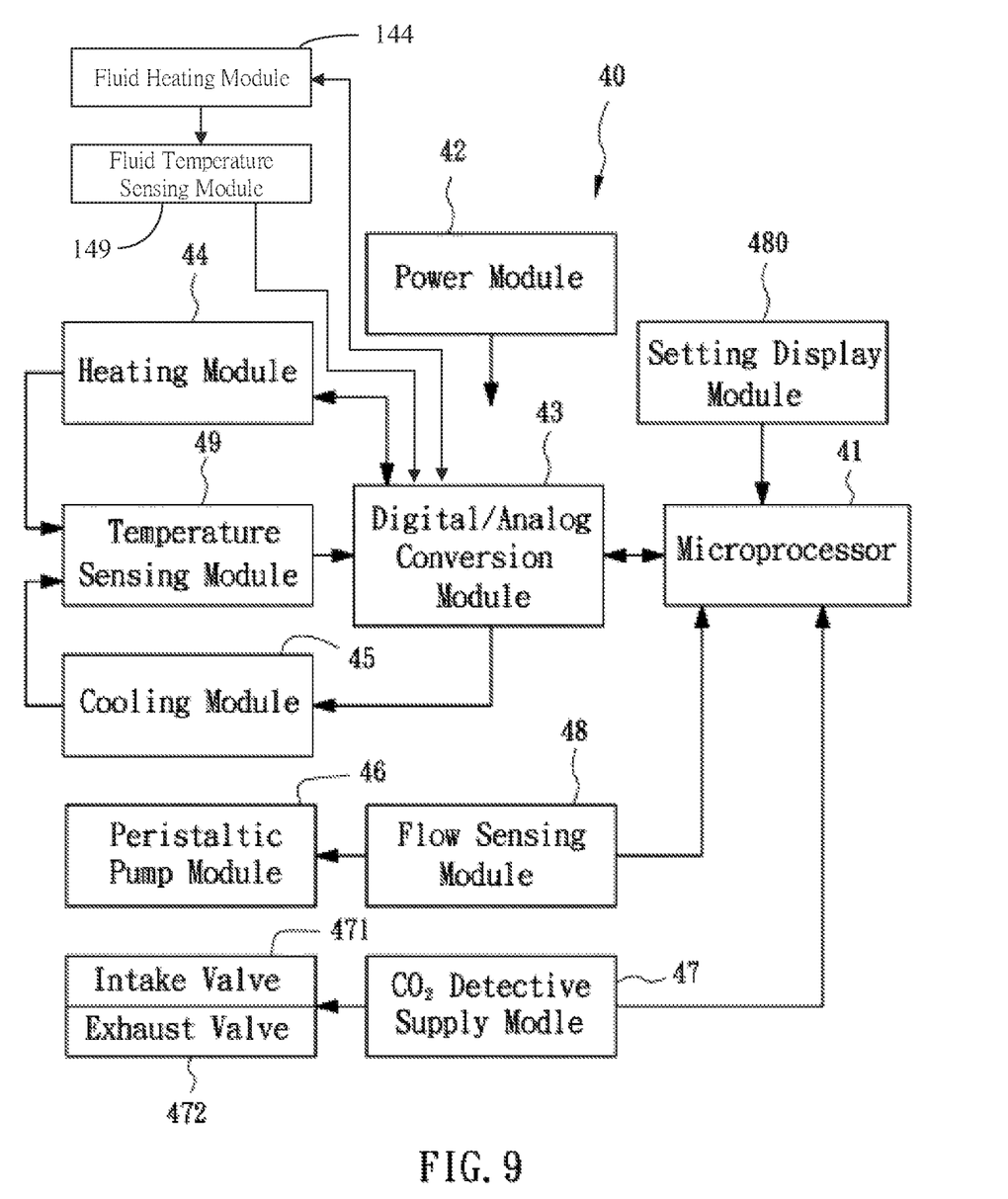
FIG. 9 is a block diagram view showing a circuit of an electric control unit of the movable cell incubator according to the preferred embodiment of the present invention.

Especially shown in FIG. 9, the electric control unit 40 is a kind of computer. In one embodiment, the microprocessor 41 may be implemented by commercial products such as Intel 8051 series microprocessor, x86 or x64 instruction set compatible processors manufactured by Intel, AMD and/or VIA Technologies, ARM instruction set compatible processors manufactured by Texas Instruments, Qualcomm and other companies. In another embodiment, the microprocessor 41 may be implemented as an ASIC (Application Specific Integrated Circuit) which contains an embedded processor. The microprocessor 41 may include system memories for storing operating system and application programs for fulfilling the operations mentioned in the present application. The system memory is also used for executing the operating system and the application. The operating system may be real-time operating systems, Android, Linux, UNIX or any other operating system. The microprocessor 41 may include interfaces for connecting with other modules mentioned above. The interfaces may include GPIO (general purpose input/output) pins, USB (Universal Serial Bus), PCI, PCI-Express, $I^2C$ and/or other industrial standard interfaces.

The power module 42 is used to supply power to the microprocessor 41 and all modules of the movable cell incubator. The power module 42 may contain a battery or a rechargeable battery for supply power during the transportation. In the laboratory and in the factory, the power module 42 can use external power source from utility. AC-DC converter, capacitors, and regulators may be required to convert AC power source to stable DC current for the internal modules. The power module 42 may further comprise DC-DC converters to convert voltages to each of the modules. Person having ordinary skill in the art is able to understand the power module 42 is quite similar to those used in the portable computers, laptop computers or controllers.

The digital/analog conversion module 43 is served to convert digital signal to analog signal or vice versa. They are often named as ADC and/or DAC. Hundreds of ADC/DAC designs can be found in the textbooks and patent publications. The microprocessor 41 may send digital/analog signals to the digital/analog conversion module 43 for transmitting corresponding analog/digital signals to the modules. Reversely, the modules may send digital/analog signals to the digital/analog conversion module 43 for transmitting corresponding analog/digital signals to the microprocessor 41.

The heating module 44 is optional and is configured to raise temperature of the culture room 13 which is monitored by a temperature sensing module 49. The microprocessor 41 receives the sensed temperature readings from the temperature sensing module 49 via the digital/analog conversion module 43. If the temperature is low enough, the microprocessor 41 may trigger the heating module 44 to heat up the culture room 13 via the digital/analog conversion module 43. As mentioned above, the heating module 44 converts electric energy supplied by the power module 42 to dissipate heats. Many resistive conductive materials can be utilized by the heating module 44.

The peristaltic pump module 46 is a type of positive displacement pump, which is also known as roller pump. The fluid is contained within a flexible pipe inside a circular pump casing. The step motor 461 with a number of rollers/shoes/wipers/lobes attached to the step motor 461. When the step motor 461 rotates, the rollers compress the flexible pipe to force the fluid to move through the pipe. There are several variations of the peristaltic pump module 46, such as hose pump, tube pump and microfluidic pumps. A person having ordinary skill in the art is able to understand the peristaltic pump module 46 can be implemented by many known ways.

With reference to FIG. 6, the cooling module 45 is disposed on an outer wall of the body 10 and includes one or more chips 451 (Thermoelectric Cooling Chip), two chilling blocks 452 corresponding to the refrigeration room 12, and one or more corresponding heat sink sets 453, wherein the cooling module 45 transfers cold source of the two chips 451 to the refrigeration room 12 via the two chilling blocks 452, and the microprocessor 41 controls a temperature of the refrigeration room 12 at 4° C. to 6° C. The chips 451, acts as a heat pump, use the Peltier effect or so-called thermoelectric cooling to create heat influx between the junctions of two different types of materials. In this application, the chips 451 create the heat influx between the chilling blocks 452 and the heat sink sets 453. Once the chips receive electric energy supplied from the power module 42, they pump heat out of the refrigeration room 12 to the heat sink sets 453 outside the body 10. Consequently, the container 100 and the cell culture media 140 in the refrigeration room 12 are cooled. Person having ordinary skill in the art can understand thermoelectric cooling or vapor-compression cooling techniques can be used by the cooling module 45.

The body 10 further includes a pump chamber 14 located beside the refrigeration room 12 and the culture room 13 so as to accommodate the peristaltic pump module 46, and the second lid 30 covers the refrigeration room 12 and the pump chamber 14. The refrigeration room 12 has a first seal 15 fixed on a top thereof, and the pump chamber 14 has a second seal 16 mounted on a top thereof so that when the second lid 30 covers the refrigeration room 12 and the pump chamber 14, it matingly contacts with the first seal 15 and the second seal 16. Referring to FIG. 5, between the culture room 13 and the first lid 20 is defined a transparent glass 70, and the culture room 13 has a third seal 17 secured on a top thereof so that when the transparent glass 70 covers the culture room 13, it matingly contacts with the third seal 17 so as to cultivate the cells in an airtight condition.

Figure 4:
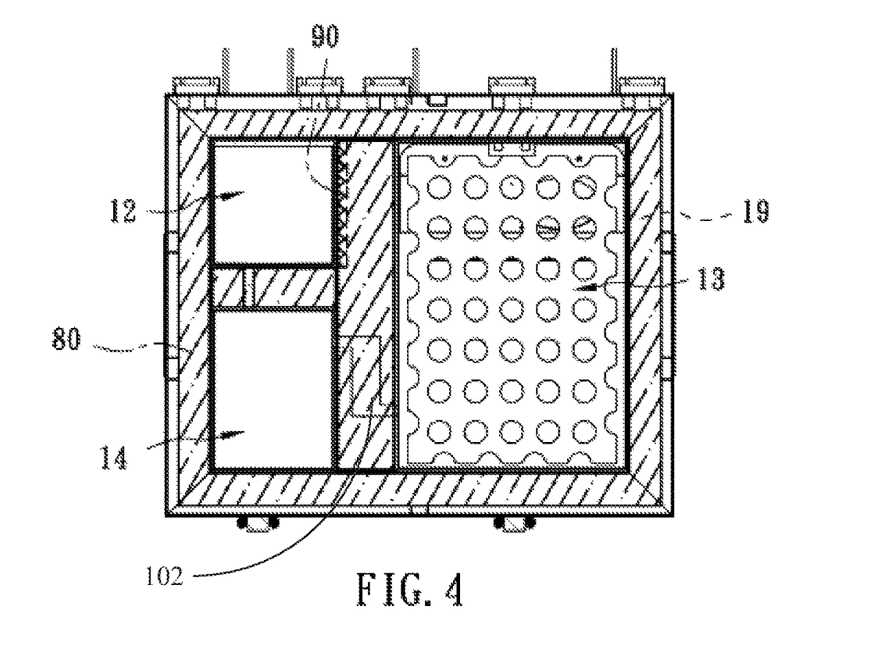
FIG. 4 is a top plan view showing the assembly of the movable cell incubator according to the preferred embodiment of the present invention.

As shown in FIG. 4, the movable cell incubator further comprises a heat insulating material 80 filled in a second internal space 19 of the refrigeration room 12, the pump chamber 14, and the culture room 13. In one embodiment, the heat insulating material 80 is made of polyethylene (PE) so as to insulate heat from the refrigeration room 12, the pump chamber 14, and the culture room 13. Between the refrigeration room 12 and the culture room 13 is defined a vacuum insulation panel 90 configured to attach on an outer wall of the refrigeration room 12, and the vacuum insulation panel 90 has a vacuum protection layer and a core filler filled inside the vacuum protection layer, the vacuum insulation panel 90 is vacuumed and is heat sealed so as to avoid air flowing and heat transferring, thus preventing a low temperature of the refrigeration room 12 influencing the culture room 13.

As shown in FIGS. 1, 2, and 5, the movable cell incubator further comprises plural first connection elements 50, plural second connection elements 51, and multiple locking sets 60 fixed on the first lid 20 and the second lid 30 and locked with the body 10, hence the first lid 20 and the second lid 30 are rotatably connected with the body 10 by way of the plural first connection elements 50 so that the first lid 20 and the second lid 30 open and close the body 10. The transparent glass 70 is rotatably connected with the body 10 by using the plural second connection elements 51 so that the transparent glass 70 and the first lid 20 are individually opened. After the first lid 20 and the second lid 30 cover the body 10, the first lid 20 and the second lid 30 are locked by the multiple locking sets 60. In one embodiment, the connection elements 50 and the second connection elements 51 are hinges or mechanical bearing that connects the body 10 and the lids 20 and 30, respectively. There are many kinds of hinges such as spring hinge, barrel hinge, pivot hinge, butt hinge, case hinge, continuous hinges, concealed hinge, Butterfly hinge, flag hinge, strap hinge, H hinge, HL hinge, . . . and etc. The body 10 and the lids 20 and 30 are connected by the connection elements 50 and 60 rotate relative to each other about a fixed axis of rotation. Thus a connection element 50 or 60 has a degree of freedom.

Figure 3:
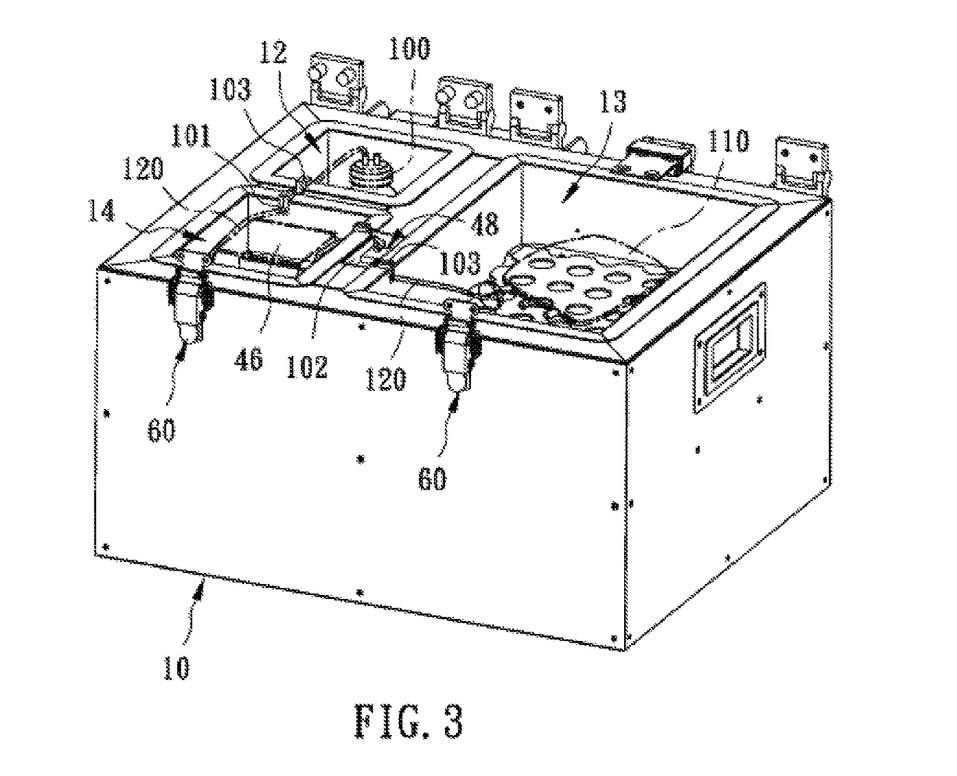
FIG. 3 is a perspective view showing the assembly of a part of the movable cell incubator according to the preferred embodiment of the present invention.

As illustrated in FIG. 3, the body 10 further includes a first through orifice 101, a second through orifice 102, and multiple protective sleeves 103, wherein the first through orifice 101 is in communication with the refrigeration room 12 and the pump chamber 14, the second through orifice 102 communicates with the pump chamber 14 and the culture room 12, and the multiple conveying tubes 120 connect with the peristaltic pump module 46 via the first through orifice 101 from the refrigeration room 12 and extend into the culture room 12 via the second through orifice 102 from the peristaltic pump module 46. In short, the cell culture media stored in the container 100 is pumped out of the refrigeration room 12 to the culture room 13 via the pump chamber 14 by the step motor 461 of the peristaltic pump module 46.

After cultivating the cells, the container 100, the at least one cell culture bag 110, the multiple protective sleeves 103, and the multiple conveying tubes 120 are connected in a sterile environment, and the container 100 is housed in the refrigeration room 12 so that a temperature of the container 100 is maintained at 4° C. to 6° C., and the multiple conveying tubes 120 are coupled with the peristaltic pump module 46 and are accommodated in the pump chamber 14, then the at least one cell culture bag 110 is placed in the culture room 13, the multiple protective sleeves 103 are fixed on the first through orifice 101 and the second through orifice 102 respectively so that the multiple conveying tubes 120 insert through the first through orifice 101 and the second through orifice 102 of the body 10 by using the multiple protective sleeves 103. Each of the multiple protective sleeves 103 is made of silicone material so as to matingly contact with each of the multiple conveying tubes 120, thus fixing each conveying tube 120 and isolating the refrigeration room 12, the culture room 13, and the pump chamber 14 effectively. Thereafter, the first lid 20 and the second lid 30 airtightly cover the refrigeration room 12, the pump chamber 14 and the culture room 13, and culture time, temperature, and humidity of the cells and output quantity of the peristaltic pump module 46 are set a by way of the setting display module 480.

With reference to FIGS. 3 and 5, the culture room 13 includes a hollow platform 131 defined therein and configured to hold the at least one cell culture bag 110, and the culture room 13 includes a water tray located below the hollow platform 131, wherein the hollow platform 131 communicates with the water tray 132 so that the water tray 132 holds sterile aqueous solution and controls the culture room 13 in a predetermined humidity as cultivating the cells.

Figure 7:
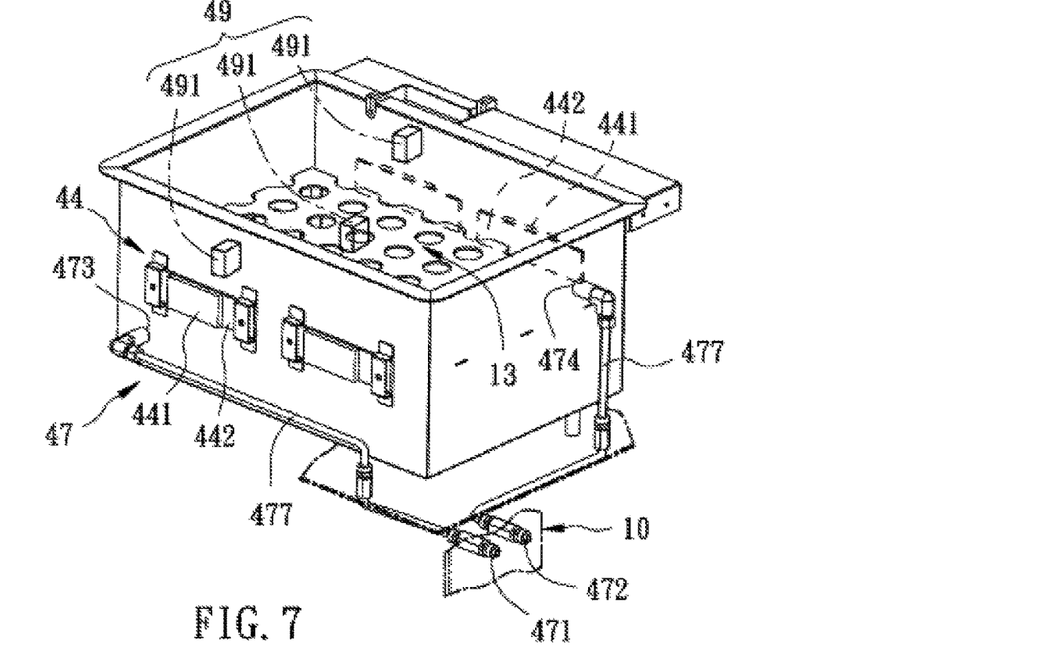
FIG. 7 is another perspective view showing the assembly of a part of the movable cell incubator according to the preferred embodiment of the present invention.

Referring to FIGS. 5 and 7, the $CO_2$ detective supply module 47 includes an intake valve 471 and an exhaust valve 472 which are arranged on the outer wall of the body 10, a first air hole 473 and a second air hole 474 which are defined on an outer wall of the culture room 13, a $CO_2$ detector 475 and an air blowing mechanism 476 which are mounted in the culture room 13. The intake valve 471 is in connection with the first air hole 473 via a connection tube 477 so as to guide $CO_2$ from an external environment, the exhaust valve 472 is coupled with the second air hole 474 via another connection tube 477 so as to release pressure. The air blowing mechanism 476 circulates air in the culture room 13, the $CO_2$ detector 475 is electrically connected with the microprocessor 41 so as to detect concentration of $CO_2$ in the culture room 13 and to control the concentration of $CO_2$ at a predetermined percentage. In this embodiment, the air blowing mechanism 476 is a fan or a blower driven by an electric motor powered by the power module 42 or the microprocessor 41. The microprocessor 41 is able to control the electric motor driving the fan or an air compressor to blow. In one embodiment, when a higher voltage is applied, the electric motor runs faster. Hence, the microprocessor 41 is able to control the air flow in the culture room 13.

The $CO_2$ detector 475 may be made of well-known detectors. For examples, U.S. Pat. Nos. 4,994,117 and 4,691,701 provide carbon dioxide detectors. Person having ordinary skill in the art is able to find suitable detector 475.

The electric control unit 40 may comprise one or more heating module 44. The power module 42 supplies the power to each of the heating module 44, and the heating module 44 may be secured on the outer wall of the culture room 13, wherein the heating module 44 includes multiple resistive heating sheets 441 and plural copper pieces 442 attached on the multiple resistive heating sheets 441 respectively.

Figure 8:
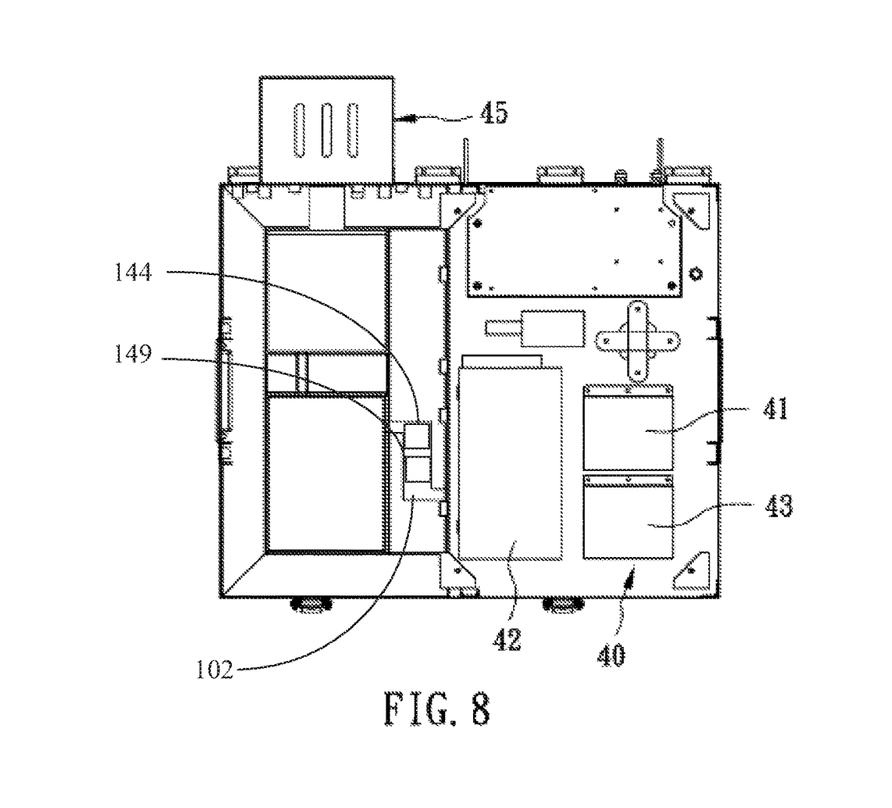
FIG. 8 is a bottom plan view showing the assembly of a part of the movable cell incubator according to the preferred embodiment of the present invention.

As shown in FIGS. 4 and 8, a fluid heating module 144 of the electric control unit 40 may be placed between the pump chamber 14 and the culture room 13. In one embodiment, the heating module 144 is placed around the second through orifice 102. Person having ordinary skill in the art can understand the fluid heating module 144 is able to convert electric energy supplied from the power module 42 to heat energy. Many resistive conductive materials can be utilized by the fluid heating module 144. In one embodiment, the fluid heating module 144 also includes multiple resistive heating sheets and plural copper pieces attached on the multiple resistive heating sheets respectively.

The fluid heating module 144 is configured to heat the culture fluid flowing through the second through orifice 102. Since the culture fluid stored in the refrigeration room 12, the temperature of culture fluid stored in the container 100 is colder than the temperature of the bag 110 stored in the culture room 13. In order to maintain the temperature of the bag 110 and keep variation of the temperature as little as possible, the culture fluid flowing through the conveying tube 120 in the second through orifice 102 may be warmed up before pumping into the bag 110.

In order to control the temperature of pumped culture fluid in the second through orifice 102, the fluid heating module 144 works with the fluid temperature sensing module 149 and the microprocessor 41. As the same as the heating module 44, the fluid heating module 144 is coupled to the digital/analog conversion module 43 for receiving a command from the microprocessor 41. The fluid temperature sensing module 149 is installed around the second through orifice 102. As the same as the temperature sensing module 49, the fluid temperature sensing module 149 outputs analog temperature value to the digital/analog conversion module 43. Thus, the digital/analog conversion module 43 converts the temperature value from the analog form into a digital form and sends it to the microprocessor 41. In case the temperature measured by the fluid temperature sensing module 149 is lower than a low threshold, corresponding program executed by the microprocessor 41 directs a digital command to the fluid heating module 144 via the digital/analog conversion module 43. After receiving the analog command, the fluid heating module 144 starts to heat the second through orifice. Reversely, if the temperature measured by the fluid temperature module 149 is higher than a high threshold, corresponding program executed by the microprocessor 41 directs another digital command to the fluid heating module 144 via the digital/analog conversion module 43. After receiving another analog command, the fluid heating module 144 ceases to dissipate heat. Consequently, the temperature of the second through orifice would be cooled down.

In one embodiment, the high threshold and the low threshold may be pre-programmed by the setting display module 480. Controlled temperature varies between the high and the low thresholds. Alternatively, in another embodiment, one target temperature with known or unknown control error margins may be pre-programmed by the setting display module 480. People with ordinary skill in the art can understand the aforementioned temperature control logic is implemented by the corresponding application program executable by the microprocessor 41. In other embodiment, the corresponding application program may implement more complicated control logic that has an input from the fluid temperature sensing module 149 and has an output to the fluid heating module 144.

In one embodiment, the second through orifice 102 comprises a metal plate or a metal trench. The conveying tube 120, the fluid temperature sensing module 149 and the fluid heating module 144 may be installed on the metal plate or inside a metal trench. Since the space of the second through orifice 102 is quite small, the fluid temperature sensing module 149 may comprises one temperature sensor, merely. The temperature sensor may be taped or disposed around the conveying tube 120.

Figure 10:
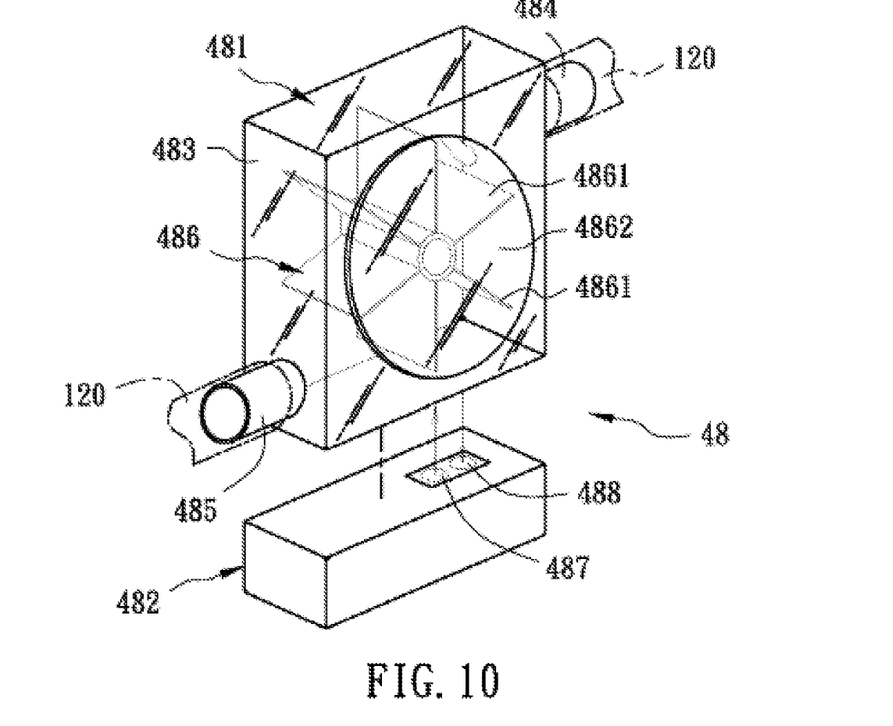
FIG. 10 is also another perspective view showing a part of the assembly of the movable cell incubator according to the preferred embodiment of the present invention.
Figure 11:
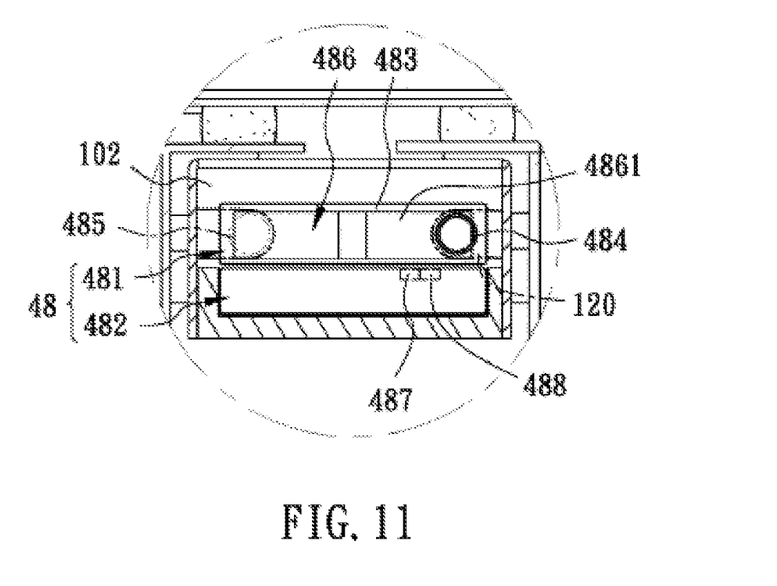
FIG. 11 is a cross sectional view showing the assembly of a part of the movable cell incubator according to the preferred embodiment of the present invention.

As shown in FIGS. 9-11, the flow sensing module 48 is coupled with the microprocessor 41 and includes a flow meter 481 and an infrared transceiver 482, wherein the flow meter 481 has a transparent casing 483, an inlet segment 484 connected to the peristaltic pump module 46, an outlet segment 485 coupled to the at least one cell culture bag 110, and a fan impeller 486 disposed on a central position of the transparent casing 483, wherein the infrared transceiver 482 has a transmitting portion 487 and a receiving portion 488 which face the fan impeller 486. The flow meter 481 is accommodated in the second through orifice 102, the infrared transceiver 482 is retained in a bottom of the second through orifice 102, and the transmitting portion 487 and the receiving portion 488 face the fan impeller 486 of the flow meter 481, hence when the fan impeller 486 rotates, it stops lights projecting to the receiving portion 488. Furthermore, because a distance between any two adjacent of plural blades 4861 of the fan impeller 486 is fixed, between any two adjacent blades 4861 is defined an interspace 4862 configured to accommodate the fluid, and a capacity (cc) of the interspace 4862 is calculated. When the multiple conveying tubes 120 convey the cell culture media 140, the infrared transceiver 482 detects a rotating speed of the fan impeller 486 via a transparent window of the flow meter 481, and after acquiring a rotating speed of the plural blades 4861 and the capacity of the interspace 4862, a message sends back to the microprocessor 41 so that the microprocessor 41 calculates and determines a supply of the cell culture media 140 to the at least one cell culture bag 110, thus controlling delivery quantity of the cell culture media 140 exactly. Preferably, the delivery quantity of the cell culture media 140 is viewed by a liquid crystal display (LCD) of the setting display module 480.

In one embodiment, the flow sensing module 48 may be located any other places between the pump chamber 14 and the culture room 13. The present application does not limit the location of the flow sensing module 48 in the second through orifice 102. The flow sensing module 48 may use other transceiver 482 working on spectrum other than infrared.

In one embodiment, the transceiver 482 may report an interrupt signal indicating the reflected light is cut by one of the rotating blades 4861 to the microprocessor 41. Application runs by the microprocessor 41 may receive the hardware interrupt signal from the transceiver 482 and calculate the delivered media volume accordingly. In another embodiment, the transceiver 482 may further include a circuit for calculating the delivered media volume or quantity and report the volume to the microprocessor 41. Application runs by the microprocessor 41 may receive the volume or quantity report from the transceiver 482.

In one embodiment, the setting display module 480 may be a touch sensitive screen which includes a screen for displaying information and a touch sensitive portion on top of the screen for receiving user's touch or gesture. Since the touch sensitive screen is widely used in the consumer electronics such as smartphone, personal digital assistant, laptop computer and smart tablet computer, a person with ordinary skill in the art can understand how the touch sensitive screen interacts with the microprocessor 41. In another embodiment, the setting display module 480 may comprises a screen for displaying information and a keyboard and/or a touch pad for receiving users' inputs. Since the screen, the keyboard and the touch pad are common output and input devices in the computing field, a person with ordinary skill in the art can understand how the screen and the keyboard and/or a touch pad interact with the microprocessor 41. The afore-described cultivating condition(s) may be input or displayed by the setting display module 480.

The electric control unit 40 further includes a temperature sensing module 49 electrically connected with the microprocessor 41 and includes one or multiple sensors 491, wherein the multiple sensors 491 may be placed on a central position of the culture room 13 and on the outer wall of the culture room 13 so as to sense interior temperature and exterior temperature of the culture room 13, respectively. Thereby, the multiple sensors 491 sense the exterior temperature and the interior temperature of the culture room 13 so as to control the temperature of the culture room 13. When the culture room 13 does not reach to a desired temperature, the microprocessor 41 starts the heating module 44 to heat the culture room 13, thus cultivating the cells at the desired temperature.

The sensor 491 may send analog signal in term of voltage or current representing temperature reading to the digital/analog conversion module 43. There are four types of temperature sensors: negative temperature coefficient thermistor, resistance temperature detector, thermocouple and semiconductor-based sensors. One person with ordinary skill in the art can understand how the sensor 491 detects temperature.

In one embodiment, there is only one sensor 491 connecting to the microprocessor 41. In case the temperature read by the sensor 491 is under a threshold, the microprocessor 41 starts one or more the heating modules 44 until the temperature reading is raised to exceed the threshold. In another embodiment, there are multiple sensors 491 connecting to the microprocessor 41. In case one temperature read by one of the sensors 491 is under the threshold, the microprocessor 41 starts one or more the heating modules 44 until all of the temperatures readings from all of the multiple sensors 491 are above the threshold. In other embodiment, using an algorithm specially tailored to the physical arrangements of the sensors 491 and the heating modules 44, the microprocessor 41 may determine whether to start one or more the heating module 44 according to all of the temperature readings from multiple sensors 491.

As shown in FIG. 9, there are two independent control loops for the heating module 44 and the fluid heating module 144, respectively. The one or more heating module 44 is designed to control the temperature of the culture room 13. Independently, the fluid heating module 144 is designed to control the temperature of the culture fluid or at least the temperature of the second through orifice 102. Logics with regard to these two independent control loops are implemented by one or two program executed by the microprocessor 41. In one embodiment, the high and low thresholds in these two control loops are different. And the thresholds in these two control loops may be displayed and/or changed by the setting display module 480.

In one embodiment, the temperature control loop for the fluid heating module 144 is not always activated. According to the configurable parameters of culturing automation mechanism, the culture fluid may be pumped several times per day, or even one timer per several days. Since the pumping culture fluid is not usually frequently, there is no need to activate the temperature control loop of the culture fluid. The application program executed by the microprocessor 41 may receive or read a configurable timing parameter related to the pumping time. For example, the timing parameter may be five or ten minutes before the pumping of culture fluid. When the pumping is going to be activated, the application program starts the temperature control loop of the culture fluid. When the pumping is finished, the application program ends the temperature control loop. It saves energy power and cools the temperature of the culture fluid remained in the second through orifice 102 and makes the culture fluid fresh. The timing parameter may be configured and displayed via the setting display module 480.

However, if the temperature of the culture fluid being pumped into the bag 110 needs to be warmer than the unpumped culture fluid stored in the container 100, the temperature control loop for the fluid heating module 144 may be configured to be activated always.

Referring to FIGS. 3 and 9, as cultivating the cells in the movable cell incubator, the electric control unit 40 controls the movable cell incubator, and the power module 42 supplies the power. Thereafter, a user sets a desired value by using the setting display module 480 so that the microprocessor 41 has calculating process, the $CO_2$ detective supply module 47 supplies $CO_2$, and the concentration of $CO_2$ in the culture room 13 is set at the predetermined percentage, the heating module 44 heats so that the culture room 13 is controlled at the desired temperature. Thereafter, the cooling module 45 supplies the cold source to the refrigeration room 12 so that the temperature of the refrigeration room 12 maintains at a predetermined value. In addition, the temperature sensing module 49 senses a temperature change and the microprocessor 41 adjusts the cell cultivating conditions randomly. The microprocessor 41 outputs signals and the signals is converted by the digital/analog conversion module 43 so as to change the rotating speed of the step motor 461, and the cell culture media 140 is delivered into the at least one cell culture bag 110 through the multiple conveying tubes 120, thus cultivating the cells in batch metering manner.

As illustrated in FIGS. 1 and 2, the body 10 further includes a plurality of grips 18 arranged on two opposite ends of the outer wall of the body 10, the first lid 20, and the third lid 30 respectively so as to carry the movable cell incubator and to open and close the first and second lids 20, 30.

Accordingly, the movable cell incubator is compact and is movable easily. Preferably, the movable cell incubator automatically cultivates the cells at designated time and quantity.

The movable cell incubator further has advantages as follows:

1. The setting display module 480 is fixed on the first lid 20 so that the user operates and sets the desired value easily by operating the LCD of the setting display module 480.

2. The first lid 20 and the transparent glass 70 are rotatably connected with the body 10 individually, hence when opening the first lid 20, the user is capable of observing the cells in the body 10 via the transparent glass 70, and the transparent glass 70 presses the third seal 17 so as to keep the airtight condition in the culture room 13.

3. The multiple resistive heating sheets 441 are controlled by the microprocessor 41 and are sensed by the multiple sensors 491 so as to exactly maintain the temperature of the culture room 13.

4. The cell culture media 140 is fed into the at least one cell culture bag 110 at an accurate quantity by way of the step motor 461.

5. The multiple protective sleeves 103 are made of the silicone material and matingly contact with each of the multiple conveying tubes 120, the multiple conveying tubes 120 insert through the pump chamber 14 from the refrigeration room 12 and then extend into the culture room 13 from the pump chamber 14 so as to avoid temperature interferences and to insulate air from the refrigeration room 12, the culture room 13, and the pump chamber 14.

6. The flow sensing module 48 is serially connected on the multiple conveying tubes 120 between the peristaltic pump module 46 and the at least one cell culture bag 110 so as to control the delivery quantity of the cell culture media 140. In addition, the supply of the cell culture media 140 is determined precisely based on the rotating speed of the fan impeller 486 and the capacity of the interspace 4862

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. A movable cell incubator, comprising:
    a body including a first internal space, a refrigeration room and an airtight culture room which are located above the first internal space, the refrigeration room being configured to accommodate a culture fluid, and the culture room accommodating at least one cell culture bag;
    a first lid rotatably connected on the body and airtightly covering the culture room;
    a second lid rotatably connected on the body adjacent to the first lid and airtightly covering the refrigeration room; and
    an electric control unit arranged on the body, and the electric control unit including a microprocessor, a power module accommodated in the electric control unit, a digital/analog conversion module defined between the microprocessor and the power module, a heating module secured on an outer wall of the culture room and controlling a temperature of the culture room, a cooling module disposed on the electric control unit on an outer wall of the body and electrically connected with electric control unit so as to supply cold source to the refrigeration room, a peristaltic pump module, a flow sensing module, a $CO_2$ detective supply module arranged in the culture room and electrically connected with the microprocessor so as to supply $CO_2$ to the culture room, and a setting display module exposing and fixed on the first lid;
    wherein the peristaltic pump module is connected between the culture fluid and the at least one cell culture bag by way of multiple conveying pipes, the flow sensing module is serially connected on the multiple conveying pipes, the power module supplies power, and the setting display module is configured to set cell cultivating conditions, the microprocessor operates and controls the cell cultivating conditions, the flow sensing module detects fluid flow, and the peristaltic pump module pumps the culture fluid into the at least one cell culture bag;
    wherein the flow sensing module is coupled with the microprocessor and includes a flow meter and an infrared transceiver, wherein the flow meter has an inlet segment connected to the peristaltic pump module, an outlet segment coupled to the at least one cell culture bag, and a fan impeller, wherein the infrared transceiver has a transmitting portion and a receiving portion which face the fan impeller.

2. The movable cell incubator as claimed in claim 1, wherein the body further includes a pump chamber located beside the refrigeration room, and the culture room accommodates the peristaltic pump module, and the second lid covers the refrigeration room and the pump chamber, the refrigeration room has a first washer fixed on a top thereof, and the pump chamber has a second washer mounted on a top thereof so that when the second lid covers the refrigeration room and the pump chamber, the second lid matingly contacts with the first washer and the second washer.

3. The movable cell incubator as claimed in claim 2, wherein the body further includes a first through orifice and a second through orifice, the first orifice is in communication with the refrigeration room and the pump chamber, the second through orifice communicates with the pump chamber and the culture room, and the multiple conveying pipes connect with the peristaltic pump module via the first through orifice from the refrigeration room and extend into the culture room via the second through orifice from the peristaltic pump module.

4. The movable cell incubator as claimed in claim 3 further comprising multiple protective sleeves respectively fitted on the multiple conveying pipes and fixed on the first through orifice and the second through orifice individually so that the multiple conveying pipes insert through the first through orifice and the second through orifice of the body by using the multiple protective sleeves, wherein each of the multiple protective sleeves is made of silicone material.

5. The movable cell incubator as claimed in claim 1, wherein the culture room includes a hollow platform defined therein and configured to hold the at least one cell culture bag, and the culture room includes a water tray located below the hollow platform.

6. The movable cell incubator as claimed in claim 1, wherein between the culture room and the first lid is defined a transparent glass, and the culture room has a third washer secured on a top thereof so that when the transparent glass covers the culture room, it matingly contacts with the third washer.

7. The movable cell incubator as claimed in claim 6, wherein the first lid is rotatably connected on a top of the body by way of plural first connection elements, and the transparent glass is rotatably connected on the top of the body by using plural second connection elements so that the transparent glass and the first lid are individually opened.

8. The movable cell incubator as claimed in claim 1, wherein the microprocessor, the power module, and the digital/analog conversion module are accommodated in the first internal space of the body.

9. The movable cell incubator as claimed in claim 1, wherein the cooling module includes at least one chip, at least one chilling block corresponding to the refrigeration room, and at least one hear sink set, wherein the cooling module transfers cold source of the at least one chip to the refrigeration room via the at least one chilling block.

10. The movable cell incubator as claimed in claim 1, wherein the power module supplies the power to the heating module, wherein the heating module includes multiple resistive heating sheets and plural copper pieces attached on the multiple resistive heating sheets, respectively.

11. The movable cell incubator as claimed in claim 1, wherein the $CO_2$ detective supply module includes an intake pipe and an exhaust pipe which are arranged on the outer wall of the body, a first air hole and a second air hole which are defined on the outer wall of the culture room, a CO2 detector and an air blowing mechanism which are mounted in the culture room, the intake pipe is in connection with the first air hole via a connection tube so as to guide $CO_2$ from an external environment, the exhaust pipe is coupled with the second air hole via another connection tube so as to release pressure, the air blowing mechanism circulates air in the culture room, and the $CO_2$ detector is electrically connected with the microprocessor so as to detect concentration of $CO_2$ in the culture room.

12. The movable cell incubator as claimed in claim 1 further comprising a temperature sensing module electrically connected with the microprocessor, and the temperature sensing module including multiple sensors, wherein one of the multiple sensors is fixed on a central position of the culture room and another of the multiple sensors is fixed on the outer wall of the culture room so as to sense interior temperature and exterior temperature of the culture room, respectively.

13. The movable cell incubator as claimed in claim 1 further comprising plural first connection elements, plural second connection elements, and multiple locking sets fixed on the first lid and the second lid and locked with the body, hence the first lid and the second lid are rotatably connected with the body by way of the plural of first connection elements, and when the first lid and the second lid cover the body, the first lid and the second lid are locked by the multiple locking sets.

14. The movable cell incubator as claimed in claim 1 further comprising a plurality of grips arranged on two opposite ends of the outer wall of the body, the first lid and the third lid respectively.

15. The movable cell incubator as claimed in claim 1, wherein the peristaltic pump has a step motor.

16. The movable cell incubator as claimed in claim 1 further comprising a heat insulating material filled in a second internal space of the refrigeration room, the pump chamber, and the culture room.

17. The movable cell incubator as claimed in claim 1 further comprising a vacuum insulation panel attached on an outer wall of the refrigeration room.

18. The movable cell incubator as claimed in claim 4 further comprising a fluid temperature sensing module and a fluid heating module installed around the second through orifice to control the temperature of the multiple conveying pipes via the second through orifice.

19. The movable cell incubator as claimed in claim 18, wherein the control of the temperature of the multiple conveying pipes begins at a configurable time before the culture fluid is pumped into the at least one cell culture bag and ends when the peristaltic pump stops pumping.

20. A movable cell incubator, comprising:
  a body, comprises:
    a culture room for accommodating a cell culture bag;
    a refrigeration room for accommodating a container of culture fluid;
    a pump chamber; and
    a first internal space located below the culture room;
  a first lid rotatably connected on the body and airtightly covering the culture room;
  a second lid rotatably connected on the body and airtightly covering the refrigeration room;
  a microprocessor, located in the first internal space;
  a setting display module, exposing and fixed on the first lid and coupled to the microprocessor, for displaying setting information and receiving cell cultivating condition from user;
  a peristaltic pump module, located in the pump chamber and coupled to the microprocessor, for connecting the container via a first conveying pipe and pump the culture fluid out of the container;
  a flow sensing module, further comprises:
    a flow meter, having an inlet segment connected to the peristaltic pump via the first conveying pipe, an outlet segment connected to the cell culture bag via a second conveying pipe, and a fan impeller which rotates by the culture fluid pumped by the peristaltic pump; and
    an infrared transceiver, coupled to the microprocessor, having a transmitting portion and a receiving portion facing the fan impeller for detecting rotation of the fan impeller in order to report culture fluid flow inside the flow meter to the microprocessor; and
  a power module, located in the first internal space, for supplying power to the microprocessor, the setting display module, the peristaltic pump module, and the flow sensing module,
  wherein the microprocessor is configured for controlling the setting display module and the peristaltic pump module according to the cell cultivating condition and the reported fluid flow.

21. The movable cell incubator as claimed in claim 20, further comprises:
  a digital/analog conversion module, located in the first internal space and coupled to the microprocessor, for converting digital signal to analog signal and vice versa, wherein the digital/analog conversion module transmits and receives digital signal from the microprocessor;
  a heating module, secured on an outer wall of the culture room and coupled to the digital/analog conversion module, for heating the culture room;
  a fluid heating module, installed around the second conveying pipe and coupled to the digital/analog conversion module, for heating the second conveying pipe;

a fluid temperature sensing module, installed around the second conveying pipe and coupled to the digital/analog conversion module, for sensing temperature of the second conveying pipe;

a cooling module, disposed on an outer wall of the body and coupled to the digital/analog conversion module, for supplying cold source to the refrigeration room;

a $CO_2$ detective supply module, arranged in the culture room and coupled to the microprocessor, for supplying CO2 to the culture room; and a temperature sensing module, having multiple sensors, wherein one of the multiple sensors is fixed on a central position of the culture room and another of the multiple sensors is fixed on the outer wall of the culture room so as to sense interior temperature and exterior temperature of the culture room, respectively, wherein the power module is further configured for supplying power to the digital/analog conversion module, the heating module, the cooling module, the $CO_2$ detective supply module, wherein the microprocessor is further configured for controlling the heating module, the fluid heating module, the cooling module, the $CO_2$ detective supply module according to the cell cultivating condition and the exterior temperature and the interior temperature of the culture room.

* * * * *